US00PP31451P2

(12) United States Plant Patent
Yosef et al.

(10) Patent No.: US PP31,451 P2
(45) Date of Patent: Feb. 18, 2020

(54) STRAWBERRY PLANT NAMED 'DANIEL'

(50) Latin Name: ***Fragaria ananassa* Duch.**
Varietal Denomination: Daniel

(71) Applicant: Efraim Yosef, Hod HaSharon (IL)

(72) Inventors: Efraim Yosef, Hod HaSharon (IL); Asaf Meizles, Hod HaSharon (IL)

(73) Assignee: Efraim Yosef, Hod HaSharon (IL)

( * ) Notice: Subject to any disclaimer, the term of this patent is extended or adjusted under 35 U.S.C. 154(b) by 0 days.

(21) Appl. No.: 16/350,314

(22) Filed: Oct. 30, 2018

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

*Primary Examiner* — Susan McCormick Ewoldt
(74) *Attorney, Agent, or Firm* — Michelle Bos Legal LLC

(57) ABSTRACT

A new and distinct strawberry plant named 'Daniel', notable for its compact growth habit, attractive color, high stolon production, early maturity, good yield and field tolerance to powdery mildew (*Podosphaera aphanis*).

6 Drawing Sheets

Latin name: *Fragaria ananassa* Duch.
Variety denomination: 'Daniel'.

BACKGROUND OF THE VARIETY

The present invention relates to a new and distinct strawberry variety named 'Daniel', also known as 'EF-165'.

The new strawberry 'Daniel' is a product of a planned breeding program conducted by the inventors in Hod Hasharon, Israel. The objective of the breeding program is to develop new strawberry varieties with quality fruits, high yields and tolerance to diseases.

'Daniel' is a result of a controlled cross made by the inventors in 2014 in Hod Hasharon, Israel of female parent 'EF-58' (not patented) and male parent 'EF-63' (not patented). Both parent varieties resulted from controlled crosses of unnamed parents.

The new strawberry plant 'Daniel' was discovered and selected by the inventors as a single flowering plant within the progeny of the stated cross in January 2015 in a controlled environment in Hod Hasharon, Israel. After its selection, the new variety was asexually propagated by stolons in a nursery located in Hod Hasharon, Israel. The new variety was extensively tested and propagated over the next several years. The testing demonstrated that the combination of characteristics as herein disclosed for the new variety are firmly fixed and retained through successive generations of asexual reproduction. The new variety reproduces true to type.

BRIEF DESCRIPTION OF THE VARIETY

'Daniel' is primarily adapted to the climate and growing conditions of the Sharon coastal plain in Israel at 32° latitude, and to similar climatic regions. This region provides the needed growing conditions of autumn with high temperatures that promote primary plant growth and early fruit production, and mild winters with moderate temperatures and many sunny days with low humidity, which helps maintain plant vigor and fruit quality during the production months.

The following traits have been repeatedly observed and determined to be unique characteristics of 'Daniel', and in combination distinguish it as a new and distinct variety:

1. Early harvest.
2. Good yield.
3. Good crop distribution.
4. Compact growth habit, resulting in easier picking.
5. Attractive color.
6. Production of numerous stolons.
7. Good tolerance to powdery mildew (*Podosphaera aphanis*).

Plants of the new strawberry variety 'Daniel' differ from plants of the parents 'EF-58' and 'EF-63' as shown in Table 1.

TABLE 1

Comparison of 'Daniel' Strawberry to Parent Varieties

| Characteristic | 'Daniel' | 'EF-58' | 'EF-63' |
|---|---|---|---|
| Fruit size | Medium-large | Medium-large | Medium |
| Fruit color | Red to dark red | Red | Red to dark red |
| Yield | High | Medium | Medium |
| Plant size | Medium | Small to medium | Medium |
| Production of stolons | Many | Medium | Medium |
| Attitude of fruiting truss | Prostrate | Prostrate | Semi-erect |

'Daniel' has been compared to the 'Rotemi' variety (U.S. Plant Pat. No. 20,970) and the 'Tamar' variety (U.S. Plant Pat. No. 11,135) and has been found to be distinct therefrom, in that the fruit of 'Daniel' is darker in color, and produces more stolons. 'Daniel' has also been compared to the 'Shaked' variety (U.S. Plant Pat. No. 20,995) and has been found to be distinct therefrom, in that 'Daniel' has been found to produce fewer stolons then 'Shaked'. 'Daniel' is picked earlier than 'Rotemi', 'Tamar' and 'Shaked'.

BRIEF DESCRIPTION OF THE PHOTOGRAPHS

The accompanying color photographs illustrate the overall appearance of typical specimens of the new strawberry variety 'Daniel', at various stages of development. The colors shown are as true as reasonably possible with color reproductions of this type, but may differ slightly from the color value cited in the botanical description, which accurately describes the color of 'Daniel'. The depicted plant and plant parts of the new strawberry variety 'Daniel' were taken in Hod Hasharon, Israel.

DETAILED BOTANICAL DESCRIPTION OF THE VARIETY

Figure 1:
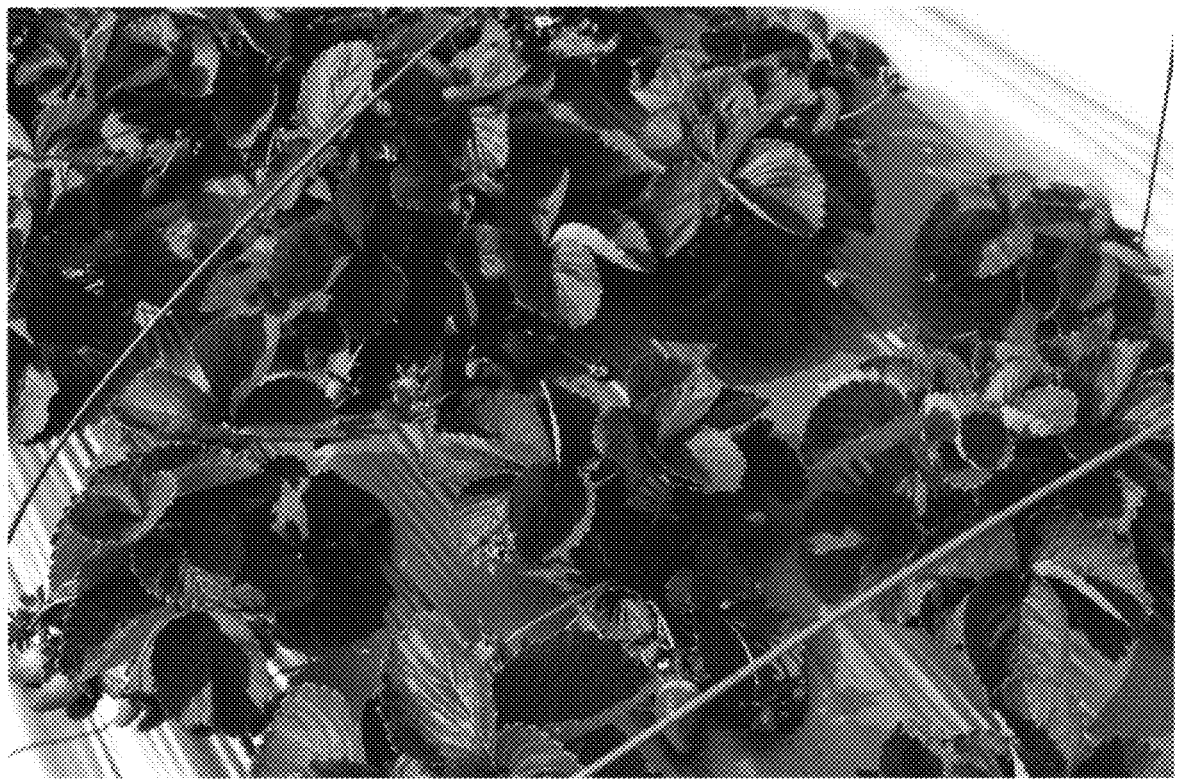
FIG. 1 shows typical fruiting field characteristics of 'Daniel' taken during November 2016.
Figure 2:
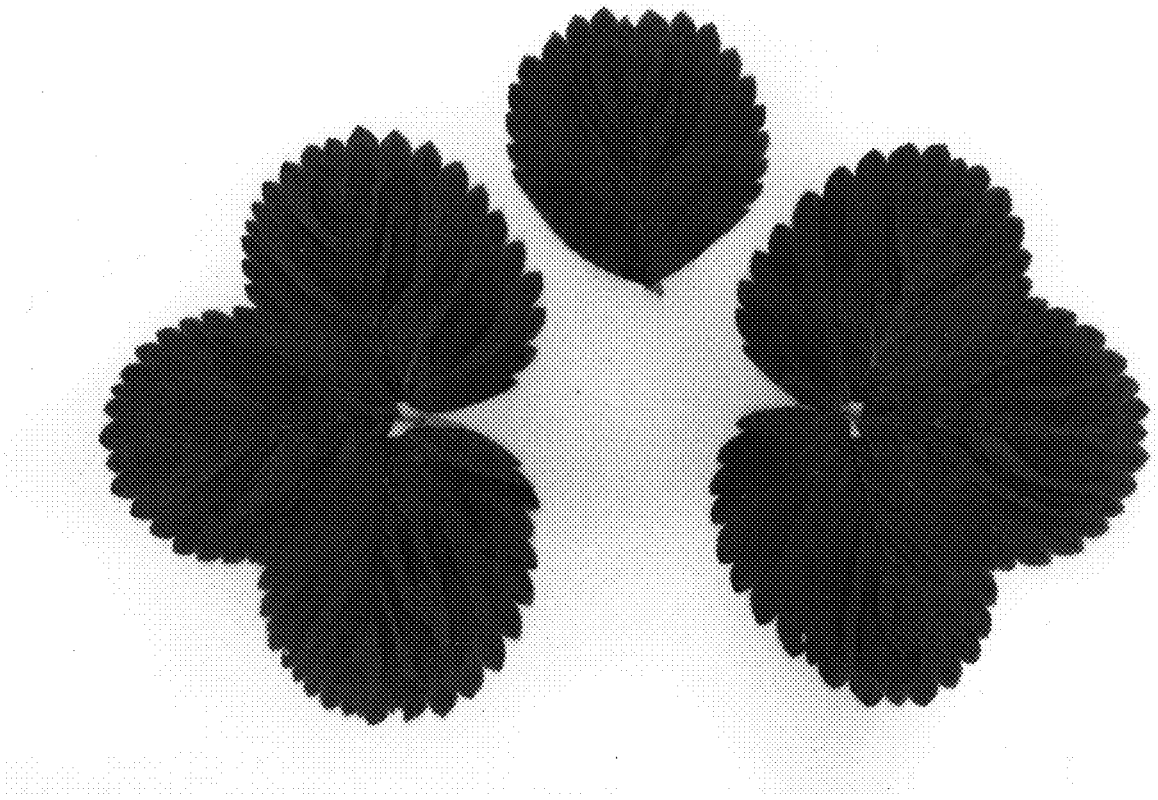
FIG. 2 shows a close up view of a typical leaf structure of 'Daniel' taken during June 2018.
Figure 3:
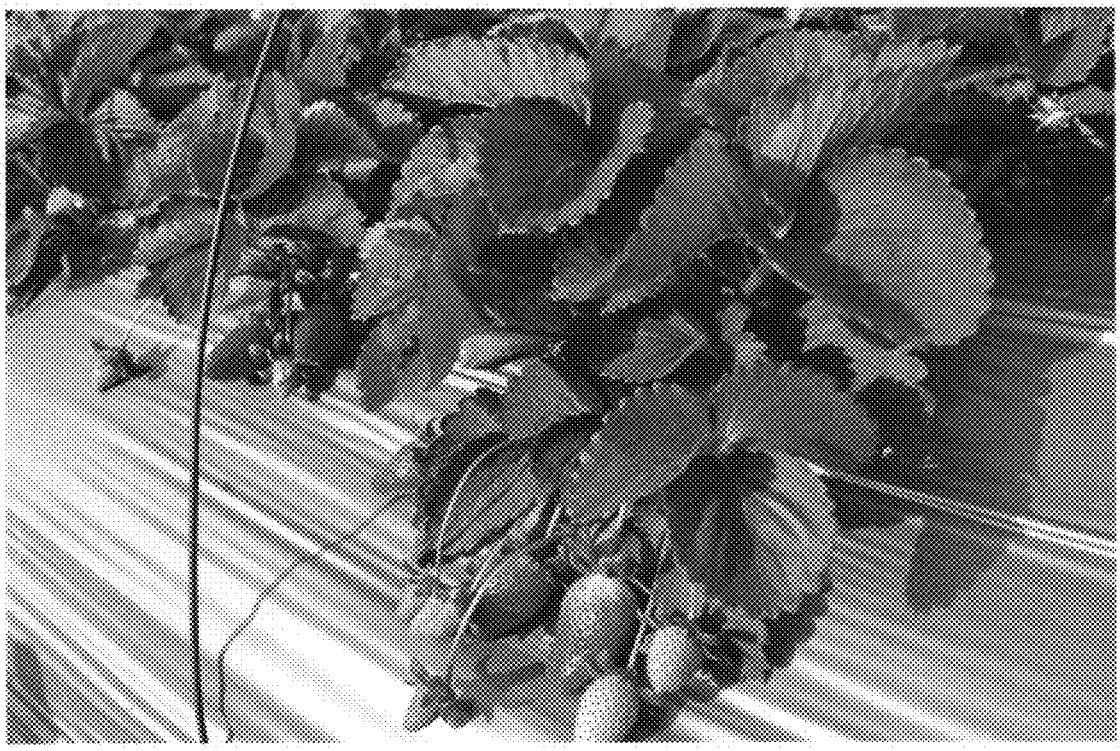
FIG. 3 shows typical mature and immature field fruit of 'Daniel' taken during November 2016.
Figure 4:
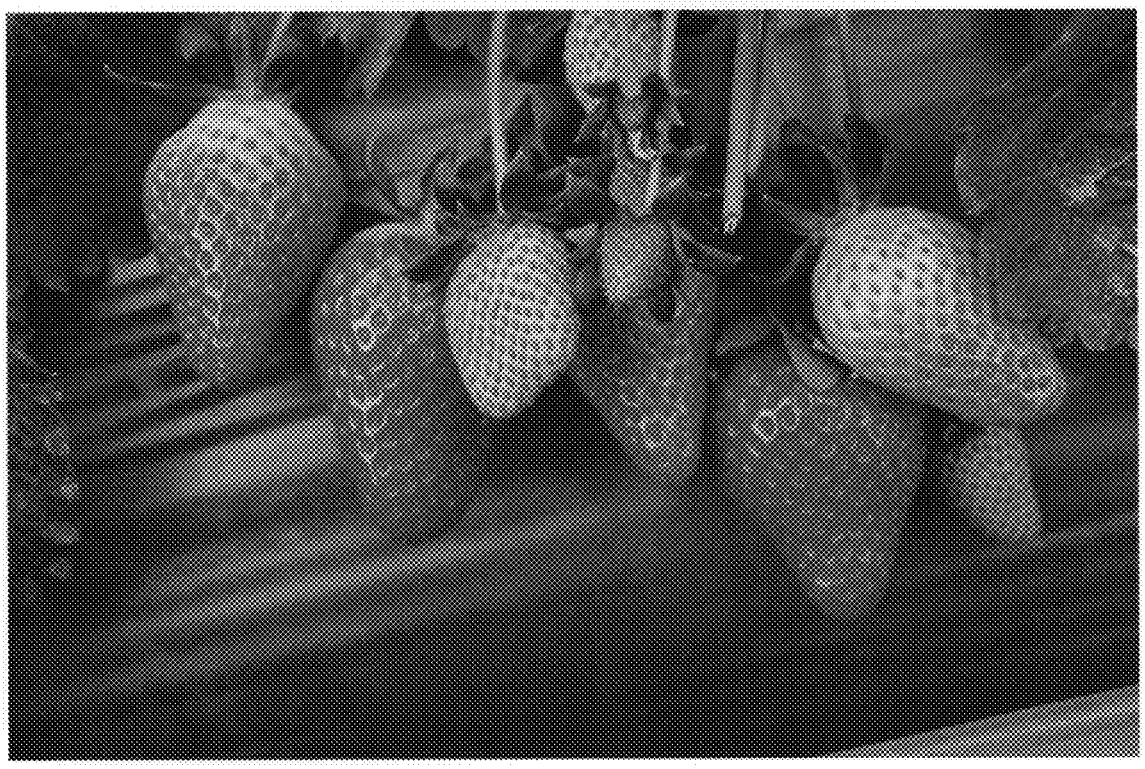
FIG. 4 shows a close-up view of mature fruit of 'Daniel' taken during February 2016.
Figure 5:
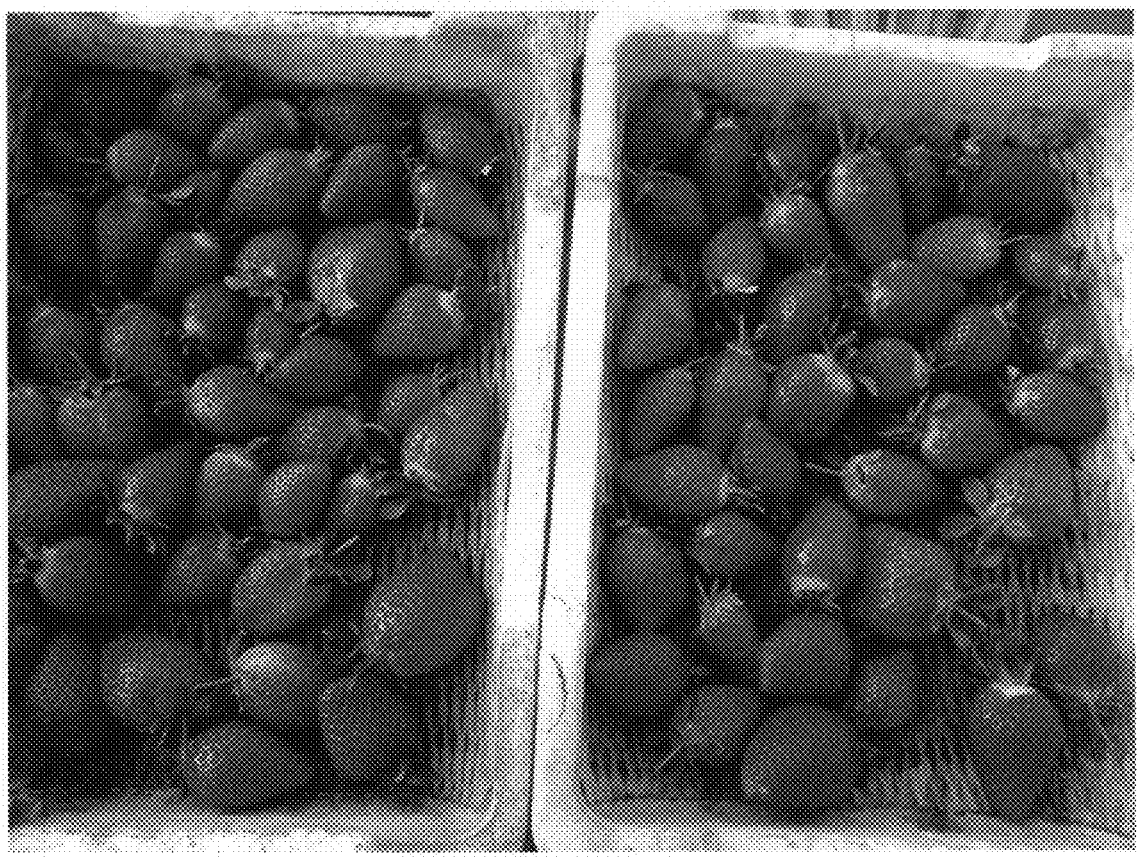
FIG. 5 shows typical external mature fruit characteristics of 'Daniel' taken during February 2017.
Figure 6:
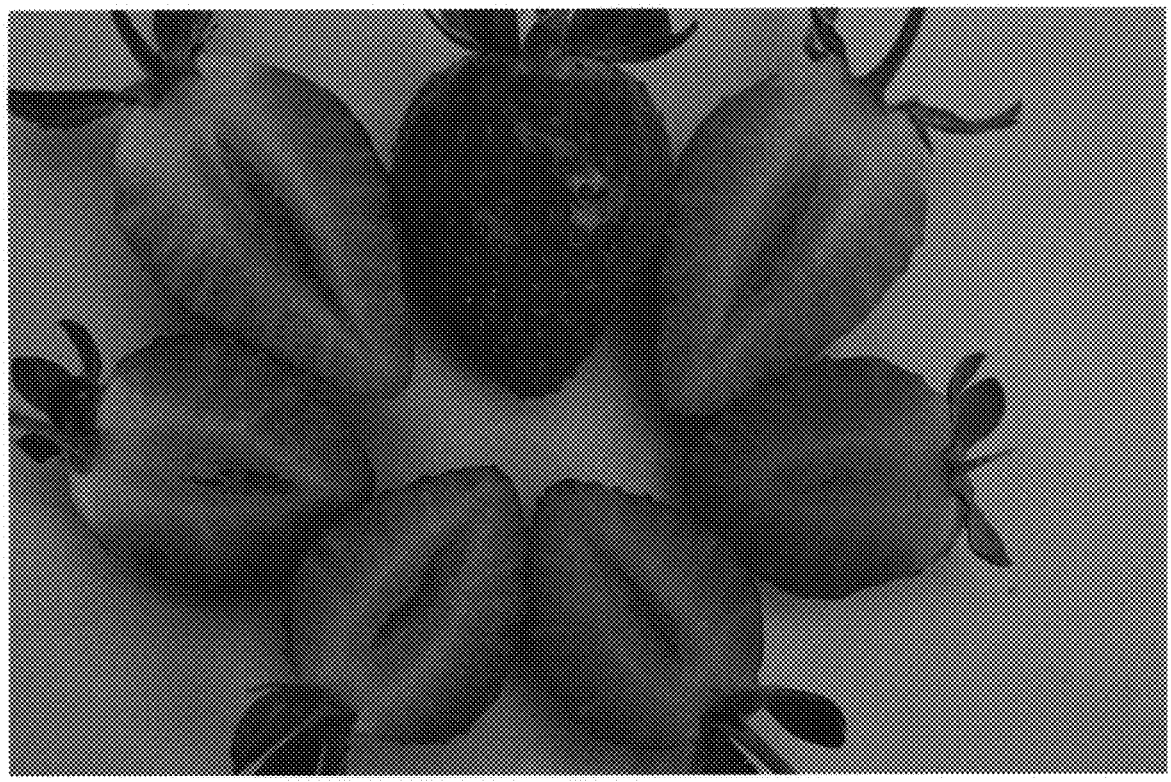
FIG. 6 shows typical internal mature fruit characteristics of 'Daniel' taken during May 2018.

The aforementioned photographs, together with the following observations, measurements and values describing the new strawberry variety 'Daniel' were taken during the 2016-2017 and 2017-2018 growing seasons in Hod Hasharon, Israel, unless otherwise noted. The described plants were grown under conditions which closely approximate those generally used in commercial practice. The characteristics of the new variety may vary in detail, depending upon variations and environmental factors, including weather (temperature, humidity and light intensity), day length, soil type and location. Quantified measurements are expressed as an average of measurements taken from a number of individual plants of the new variety. The measurements of any individual plant or any group of plants of the new variety may vary from the stated average. All colors are described according to The Royal Horticultural Society Colour Chart (6th edition, 2015).

Growing conditions at the nursery: Mother plants were planted in the beginning of May in the field nursery at 2.5 m×2.5 m spacing. A combination of overhead and drip irrigation with the addition of fertilizers was used. The average day/night temperatures during the establishment of the daughter plants, between June and August, were 32° C. and 18° C. respectively. Runners appeared beginning in June and produced daughter plants until mid-September. The daughter plants were then collected and planted directly in the field.

Growing conditions at the fruit production field: The bare-rooted plants were rinsed, dipped in Octav (prochloraz-manganese) 2 g/L solution to avoid anthracnose, and then planted in raised beds with overhead irrigation in four rows at 30 cm apart. Distance between plants within rows was 32 cm. No fertilizers were added during the first month, due to the addition of 60 to 100 $m^3$/hectare compost during field preparation. About four weeks after planting the beds were covered with silvery-black 30-micron polyethylene. The young plants were pulled out through the pre-prepared holes. From this point on the plants were irrigated with a drip system with a supply of additional fertilizers, as are typically used in agricultural practice. By the end of October, the beds were covered with transparent, 80-micron thick polyethylene tunnels.

Maximum average daytime temperatures during the cultivation season range from about 31° C. to 33° C. in August, decreasing to about 16° C. to 18° C. in January, and increasing to about 19° C. to 23° C. in March. Minimum average daytime temperatures range from about 21° C. to 25° C. in August, decreasing to about 7° C. to 10° C. in January, and increasing to about 9° C. to 13° C. in March. (Data taken from maximum and minimum average monthly temperatures at Bet-Dagan, Israel, during the period 2002 to 2013.)

Fruit:

*Color of mature fruit.*—Red N45A.
*Color of internal flesh.*—Red 44A, 43B and white 155B.
*Length.*—50 mm to 60 mm.
*Width.*—35 mm to 42 mm.
*Ratio length/width.*—Longer than broad.
*Calyx diameter.*—30 mm to 35 mm.
*Average weight.*—28 g.
*Achene color.*—Yellow green N144A.
*Number of achenes per berry.*—232 to 320.
*Achene size.*—Average 1.2 mm.
*Weight of* 1000 *achenes.*—About 0.485 g.
*Marketable yield* (*grams/plant*).—About 950 g.
*Relative size.*—Medium to large.
*Predominant shape.*—Conical.
*Difference in shapes between primary and secondary fruit.*—Slight.
*Band without achenes.*—Narrow.
*Unevenness of surface.*—Weak.
*Evenness of color.*—Even.
*Glossiness.*—Medium-strong.
*Insertion of achenes.*—Above the surface.
*Insertion of calyx.*—Level.
*Attitude of the calyx.*—Reflexed.
*Size of calyx in relation to fruit diameter.*—Same size.
*Adherence of calyx.*—Strong.
*Firmness of flesh.*—Medium.
*Hollow center expression.*—Medium.
*Flavor.*—Good.
*Soluble solids* (% *brix*).—7.5 to 9.
*Time of first flowering.*—Early, from mid-October.
*Time of first harvesting.*—Early, from mid-November.
*Harvest period.*—November to June.
*Type of bearing.*—Partially remontant.

Plant:

*Height.*—15 cm to 18 cm.
*Spread.*—25 cm to 30 cm.
*Relative size.*—Medium.
*Habit.*—Flat.
*Density.*—Medium.
*Vigor.*—Medium.

Stolon characteristics:

*Average number per plant.*—Many to very many, ranging from 100 (grown in soil-less medium) to 900 (grown in soil).
*Green color.*—Yellow green N145A.
*Anthocyanin.*—intensity Medium.
*Diameter.*—2 mm to 3 mm.
*Length.*—10 cm to 40 cm.
*Pubescence.*—Scant to medium.

Foliage characteristics:

Leaf:

*Color of upper surface.*—Green NN137A.
*Color of underside.*—Green 138B.
*Shape in cross section.*—Slightly concave.
*Interveinal blistering.*—Weak.
*Glossiness.*—Medium.
*Number of leaflets.*—Three only.

Terminal Leaflet:

*Length.*—70 mm to 80 mm.
*Width.*—65 mm to 75 mm.
*Length/width ratio.*—Slightly longer than wide.
*Serrations/leaf.*—19 to 24.
*Relative size.*—Medium.
*Shape of base.*—Rounded.
*Shape of teeth.*—Rounded-serrate.

Petiole:

*Length.*—9 cm to 15 cm.
*Diameter.*—About 3 mm.
*Petiole color.*—Yellow green 145A.
*Petiolule length.*—5 mm to 9 mm.
*Petiolule color.*—Yellow green 145A.
*Pubescence.*—Scant to medium.
*Attitude of hairs.*—Outwards.

Stipule:

*Length.*—12 mm to 16 mm.
*Width.*—5 mm to 7 mm.
*Anthocyanin coloration.*—Absent.
*Color.*—Yellow green 145A.

Fruiting truss characteristics:

*Length.*—About 9 cm.
*Position relative to foliage.*—At same level.
*Pubescence.*—Scant to medium.
*Anthocyanin intensity.*—None.
*Attitude at first pick.*—Prostrate.
*Color.*—Yellow green 145A.

Flower characteristics:

*Mature petal color — upper surface.*—White 155B, 155C.
*Mature petal color — lower surface.*—White 155C.
*Petal shape overall.*—Rounded.
*Petal apex.*—Rounded.
*Petal base.*—Rounded.
*Petal length.*—9 mm to 12 mm.
*Petal width.*—8 mm to 12 mm.
*Petal length/width ratio.*—Almost the same, slightly longer than wide.
*Number of petals per flower.*—5 to 6, sometimes more.
*Mature sepal color — upper surface.*—Green 137A.
*Mature sepal color — lower surface.*—Green 138C.
*Sepal shape.*—Obovate.
*Sepal length.*—13 mm to 17 mm.
*Sepal width.*—6 mm to 9 mm.
*Sepal length/width ratio.*—Longer than wide.
*Number of sepals per flower.*—10 to 12.
*Corolla diameter.*—22 mm to 30 mm.
*Calyx diameter.*—20 mm to 30 mm.
*Size of calyx relative to corolla.*—Almost the same.
*Size of inner calyx relative to outer calyx.*—Almost the same.
*Relative position of petals.*—Sometimes touching, sometimes overlapping.
*Stigma color.*—Yellow green 154B.
*Stamen quantity.*—25.
*Anther length.*—0.9 mm average.
*Anther color.*—Greyed-orange 163B.
*Filament length.*—1 mm to 3 mm.
*Filament color.*—Yellow green 150C.

Disease resistance: Field tolerance to powdery mildew (*Podosphaera aphanis*).

The invention claimed is:

1. A new and distinct strawberry plant substantially as described and illustrated herein.

* * * * *